United States Patent
Zhong

(10) Patent No.: US 11,533,899 B2
(45) Date of Patent: Dec. 27, 2022

(54) MOSQUITO REPELLER WITH GOOD MOSQUITO KILLING EFFECT

(71) Applicant: Lefen (Shenzhen) Industrial Co., Ltd., Shenzhen (CN)

(72) Inventor: Daikuan Zhong, Shenzhen (CN)

(73) Assignee: Lefen (Shenzhen) Industrial Co., Ltd., Shenzhen (CN)

( * ) Notice: Subject to any disclaimer, the term of this patent is extended or adjusted under 35 U.S.C. 154(b) by 411 days.

(21) Appl. No.: 16/825,614

(22) Filed: Mar. 20, 2020

(65) Prior Publication Data
US 2020/0305407 A1  Oct. 1, 2020

(30) Foreign Application Priority Data
Mar. 28, 2019 (CN) .......................... 201920411781.1

(51) Int. Cl.
*A01M 1/20* (2006.01)
*A61L 9/03* (2006.01)

(52) U.S. Cl.
CPC ........... *A01M 1/2077* (2013.01); *A61L 9/035* (2013.01); *A61L 9/037* (2013.01); *A01M 2200/012* (2013.01); *A61L 2209/135* (2013.01)

(58) Field of Classification Search
CPC ........ A01M 1/2027; A61L 9/035; A61L 9/02; A61L 9/037
See application file for complete search history.

(56) References Cited

FOREIGN PATENT DOCUMENTS

CN     102740899 A  * 10/2012  ............. A61L 9/035
WO     WO89/07394   *  8/1989

* cited by examiner

*Primary Examiner* — Robert A Hopkins
(74) *Attorney, Agent, or Firm* — Cooper Legal Group, LLC

(57) ABSTRACT

A mosquito repeller includes a casing, a mosquito repellent liquid bottle, and a first heating element installed in the casing. The first heating element includes a first heat-generating body and a cotton swab. The first heat-generating body is inserted into the cotton swab, and an end of the cotton swab away from the first heat-generating body extends into the mosquito repellent liquid bottle. Since the first heat-generating body is inserted into the cotton swab, heat is concentrated at the center of the cotton swab, and the cotton swab is heated uniformly, and the vaporization of the mosquito repellent liquid is stable to improve the mosquito repelling effect of the mosquito repeller, while reducing the power consumption of the mosquito repeller, saving energy, avoiding a temperature rise of components near the heat-generating components, retarding the ageing of components, and extending the service life of the mosquito repeller.

7 Claims, 3 Drawing Sheets

MOSQUITO REPELLER WITH GOOD MOSQUITO KILLING EFFECT

FIELD OF THE INVENTION

The present invention relates to a mosquito repeller, and more particularly to the mosquito repeller effect.

BACKGROUND OF THE INVENTION

In general, a mosquito repeller requires heating a mosquito repellent liquid in order to vaporize the mosquito repellent liquid. Present existing mosquito repellent liquids are heated by using a heating ring to heat up a cotton swab, and the heating ring has a heat-generating body embedded into a certain position of the ring and provided for the heating purpose. After the heat-generating body generates heat and heats up the cotton swab through the ring, but the temperature of the ring will be uneven. In other words, the position near the heat-generating body has a high temperature, and the position away from the heat-generating body has a low temperature. During use, it is necessary to sheath the heating ring on the periphery of the cotton swab. Since the cotton swab is heated partially or heated non-uniformly, therefore only the mosquito repellent liquid situated in a small range of the cotton swab is heated and vaporized, so that the vaporization effect is poor. In the circular design of the heating ring, the heat-generating body installed in the heating ring also heats up components around the heating ring or even increases the temperature of the casing of the mosquito repeller while heating the heating ring. As a result, the heat cannot be concentrated on the cotton swab, heat energy is wasted, components nearby may be aged faster, and the service life of the product is shortened.

SUMMARY OF THE INVENTION

In view of the aforementioned drawbacks of the conventional mosquito repeller, it is a primary objective of the present invention to provide a mosquito repeller with the features of good mosquito killing effect, low power consumption, and long service life To achieve the aforementioned and other objectives, the present invention discloses a mosquito repeller effect, comprising a casing, a mosquito repellent liquid bottle, and a first heating element installed in the casing, characterized in that the first heating element further comprises a first heat-generating body and a cotton swab, and the first heat-generating body is inserted into the cotton swab, and the cotton swab extends from an end away from the first heat-generating body into the mosquito repellent liquid bottle.

In a preferred embodiment, the mosquito repeller further comprises a fragrance liquid bottle, and a second heating element installed to the casing and extending into the fragrance liquid bottle.

In a preferred embodiment, the mosquito repellent liquid bottle is coupled to the casing by a screw.

In a preferred embodiment, the casing has a fastener, and the fastener has a first elastic plate and a second elastic plate which are provided for the clamping cotton swab.

In a preferred embodiment, the casing has a through hole provided for an end of the cotton swab away from the mosquito repellent liquid bottle to be exposed from the casing.

In a preferred embodiment, the casing comprises a first body, a second body, and a third body, and the first body has an end coupled to the second body and the other end coupled to the third body, and the mosquito repellent liquid bottle is disposed between the second body and the third body.

In a preferred embodiment, the mosquito repeller further comprises the mosquito repeller further comprises a control circuit installed in the casing, and the control circuit comprises a switch tube Q1, a switch tube Q2 and a processor U1, and the first heat-generating body has an end coupled to an external power supply the other end grounded by the switch tube Q1, and the second heat-generating body has an end coupled to the external power supply and the other end grounded by the switch tube Q2, and the processor U1 is provided for controlling the connection and disconnection of the switch tube Q1 and the switch tube Q2.

In a preferred embodiment, the control circuit further comprises a potentiometer RT1 and an analog-to-digital conversion module, the potentiometer RT1 has an output terminal coupled to an input terminal of the processor U1 through the analog-to-digital conversion module, and the processor U1 connects or disconnects the resistance control switch tube Q1 and switch tube Q2 based on the potentiometer RT1.

The present invention has the following advantageous effects: With the first heat-generating body inserted into the cotton swab, the cotton swab can be heated more uniformly to improve the mosquito repelling effect of the mosquito repeller. In addition, the first heat-generating body heats up the cotton swab by concentrating the heat at the interior of the cotton swab to reduce the power consumption of the mosquito repeller and saving energy resources effectively. Further, the invention can avoid increasing the temperature of the components near the heat-generating components to achieve the effects of retarding the ageing of the components and extending the service life of the product.

Figure 1:
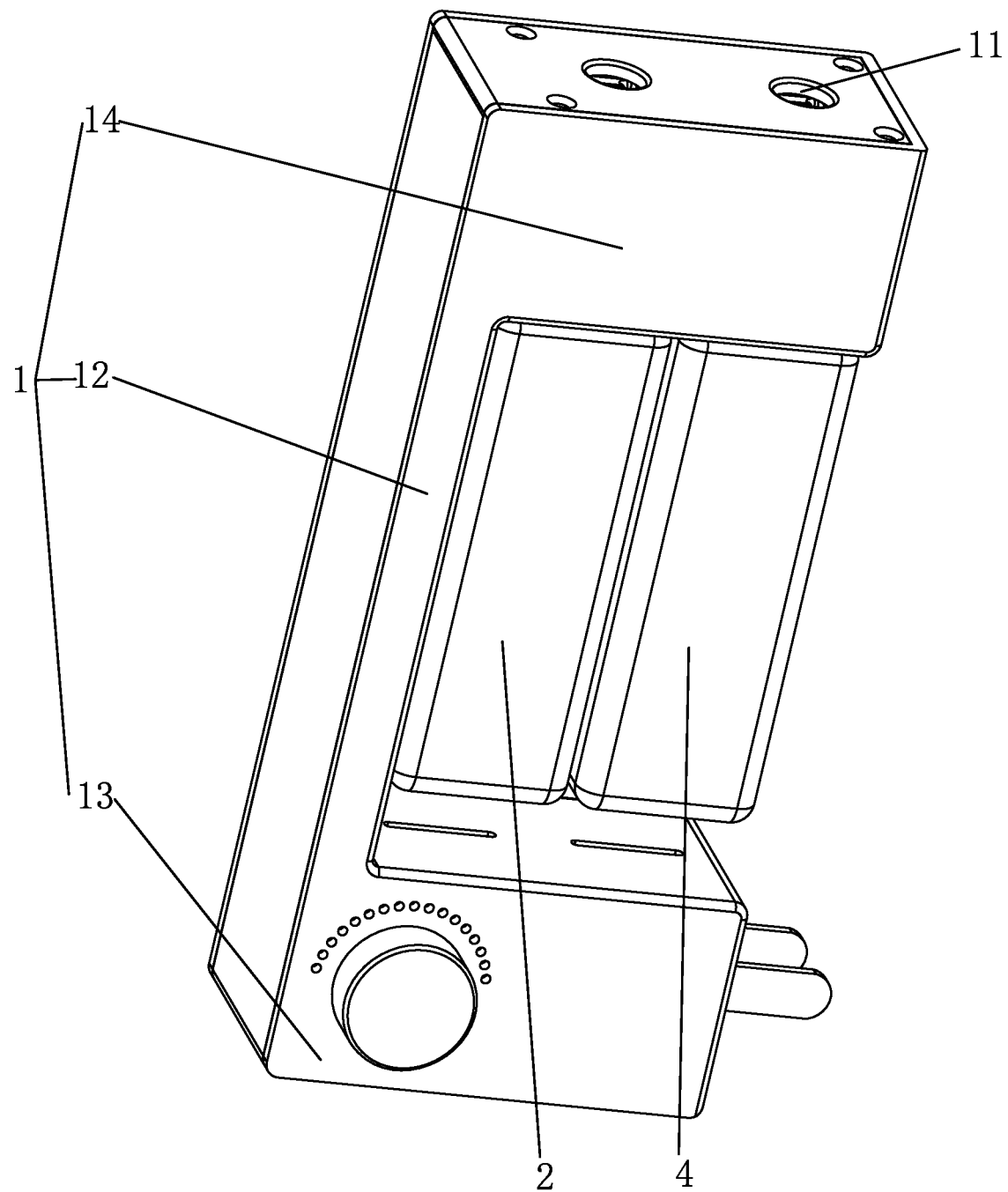
FIG. 1 is a perspective view of a mosquito repeller of the present invention.

Brief Description of Numerals Used in the Drawings: 1: Casing; 11: Through hole; 12: First body; 13: Second body; 14: Third body; 2: Mosquito repellent liquid bottle; 3: First heating element; 31: First heat-generating body; 32: Cotton swab; 4: Fragrance liquid bottle; 5: Second heating element; 51: Second heat-generating body; 6: fastener; 61: First elastic plate; 62: Second elastic plate; 7: Control circuit.

DESCRIPTION OF THE PREFERRED EMBODIMENTS

The technical contents of the present invention will become apparent with the detailed description of preferred embodiments accompanied with the illustration of related drawings as follows. It is intended that the embodiments and figures disclosed herein are to be considered illustrative rather than restrictive.

Figure 2:
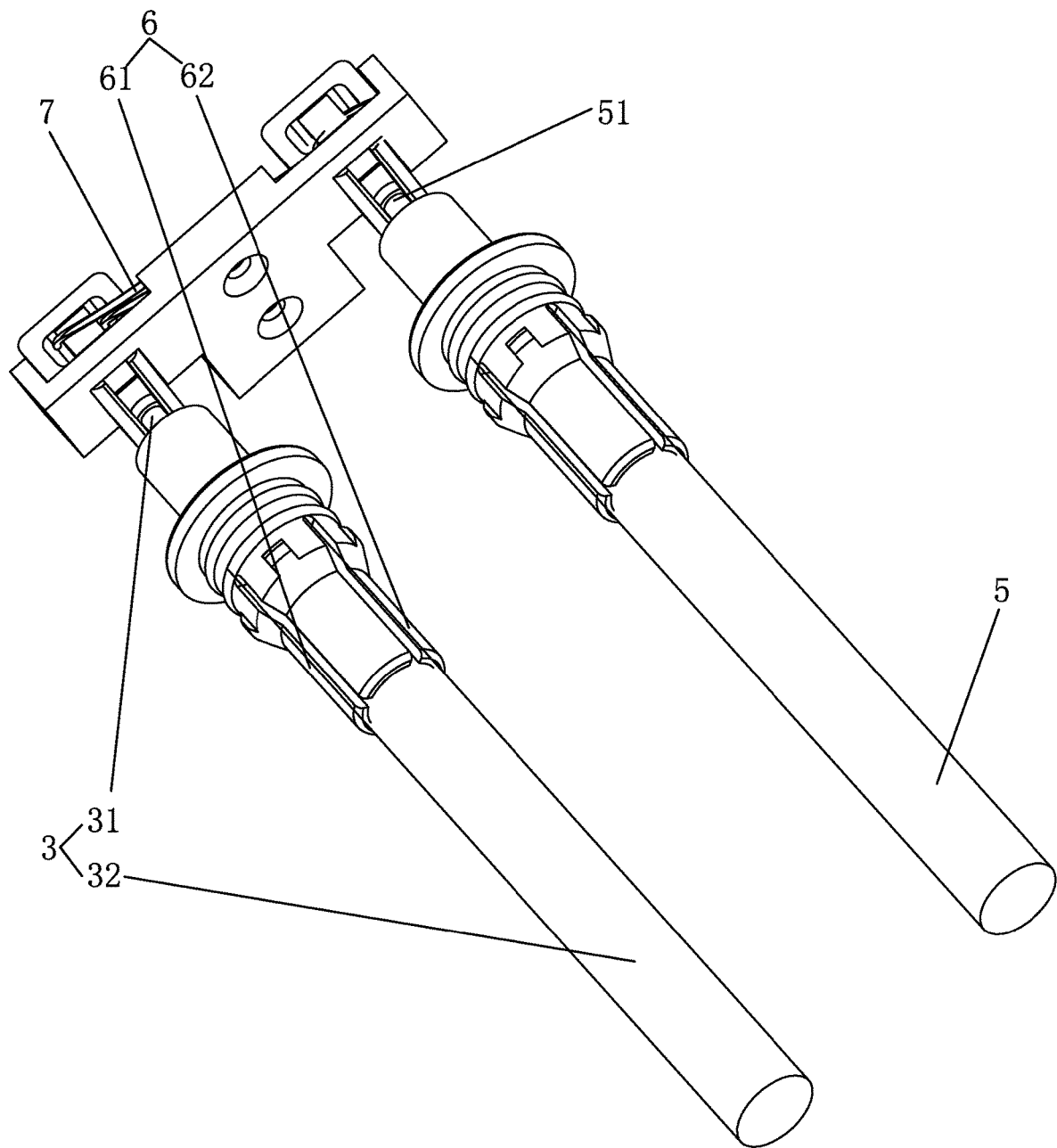
FIG. 2 is a perspective view of a mosquito repeller of the present invention without showing its casing, mosquito repellent liquid bottle, and fragrance liquid bottle.

With reference to FIGS. 1 and 2 for a mosquito repeller with a good mosquito killing effect, comprising: a casing 1, a mosquito repellent liquid bottle 2, and a first heating element 3 installed to the casing 1, characterized in that the first heating element 3 comprises a first heat-generating body 31 and a cotton swab 32, and the first heat-generating body 31 is inserted into the cotton swab 32, and an end of the cotton swab 32 away from the first heat-generating body 31 extends into the mosquito repellent liquid bottle 2.

The first heat-generating body 31 is inserted into the cotton swab 32, so that even if the first heat-generating body 31 is designed to be relatively longer, it will not be in direct contact with the mosquito repellent liquid while allowing the cotton swab 32 to be heated uniformly to vaporize the mosquito repellent liquid. In the present invention, the first heat-generating body 31 is inserted into the cotton swab 32, so that the cotton swab 32 can be heated more uniformly to improve the mosquito repelling effect of the mosquito repeller; and the first heat-generating body 31 concentrates heating the interior of the cotton swab 32 to reduce the power consumption of the mosquito repeller effectively and save energy resources. The invention also has the effect of avoiding the rise of temperature of the heat-generating components, retarding the ageing of the components and extending the service life of the product.

In FIGS. 1 and 2, the mosquito repeller further comprises a fragrance liquid bottle 4 and a second heating element 5 installed to the casing 1, and the second heating element 5 extends into the fragrance liquid bottle 4. The present invention also has an aromatherapy function. Since permethrin contained in the mosquito repellent liquid is slightly poisonous, therefore users can detoxify the permethrin in air after a mosquito repelling process, so as to reduce the harm of permethrin to the human body.

In FIG. 1, the mosquito repellent liquid bottle 2 is coupled to the casing 1 by a screw to facilitate users to refill the mosquito repellent liquid or replace the mosquito repellent liquid bottle 2.

In FIG. 2, the casing 1 has a fastener 6, and the fastener 6 comprises a first elastic plate 61 and a second elastic plate 62 which are provided for clamping the cotton swab 32, and facilitating the users to install or remove the cotton swab 32.

In FIG. 1, the casing 1 has a through hole 11 provided for allowing an end of the cotton swab 32 away from the mosquito repellent liquid bottle 2 to be exposed from the casing 1 and facilitating the mosquito repellent liquid to vaporize out of the casing 1.

In FIG. 1, the casing 1 comprises a first body 12, a second body 13, and a third body 14, and the first body 12 has an end coupled to the second body 13 and the other end coupled to the third body 14, and the mosquito repellent liquid bottle 2 is disposed between the second body 13 and the third body 14. The first body 12 can protect the mosquito repellent liquid bottle 2 to prevent the mosquito repellent liquid bottle 2 from being collided. In the meantime, the users can remove the mosquito repellent liquid bottle 2 from a side of the first body 12 in order to refill the mosquito repellent liquid or replace the mosquito repellent liquid bottle 2.

Figure 3:
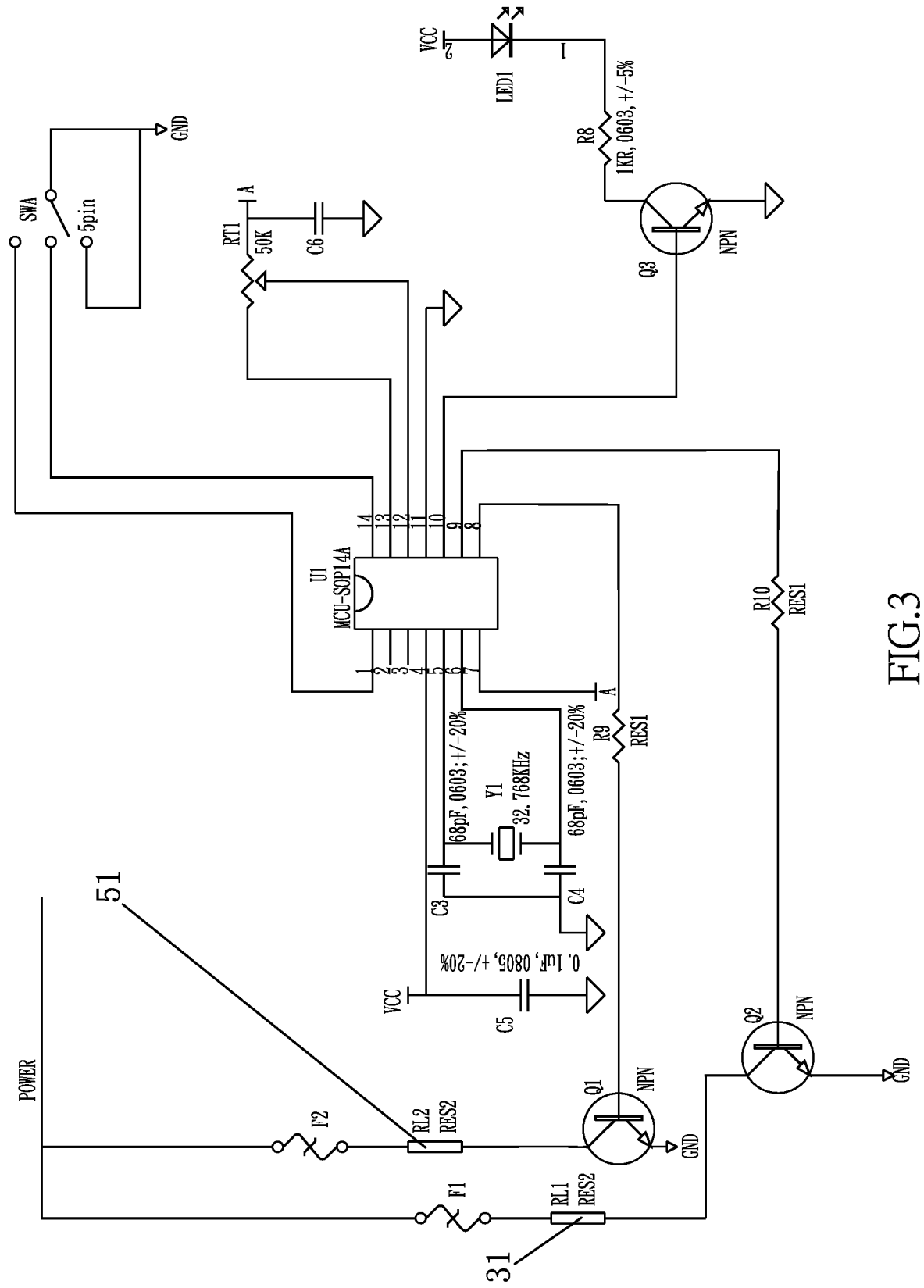
FIG. 3 is a schematic circuit diagram of a control circuit of the present invention.

In FIGS. 2 and 3, the second heating element 5 has a second heat-generating body 51, and the mosquito repeller further comprises a control circuit 7 installed in the casing 1, and the control circuit 7 comprises a switch tube Q1, a switch tube Q2, and a processor U1, and the first heat-generating body 31 has an end coupled to an external power supply and the other end grounded by the switch tube Q1, and the second heat-generating body 51 has an end coupled to the external power supply and the other end grounded by the switch tube Q2, and the processor U1 is provided for controlling the connection and disconnection of the switch tube Q1 and the switch tube Q2. The processor U1 has a control signal stored therein. In a first time period, the processor U1 controls the switch tube Q1 to be connected and the switch tube Q2 to be disconnected, so that the first heat-generating body 31 heats the mosquito repellent liquid to vaporize the mosquito repellent liquid, and the mosquito repeller is situated at a mosquito repelling operation status. In a second time period, the processor U1 controls the switch tube Q2 to be connected and the switch tube Q1 to be disconnected, so that the second heat-generating body 51 heats the fragrance liquid to vaporize the fragrance liquid, and the mosquito repeller is situated at an aromatherapy operation status. In a third time period, both of the switch tube Q1 and the switch tube Q2 are disconnected, so that the first heat-generating body 31 and the second heat-generating body 51 do not perform the heating operation. The present invention uses the processor U1 to control the connection and disconnection of the switch tube Q1 and the switch tube Q2 according to the control signal of the processor U1, so that the mosquito repeller can switch its operation status according to time and uses the aromatherapy function to achieve the detoxification effect, and the processor U1 is specific an ARM processor.

In FIG. 3, the control circuit 7 further comprises a potentiometer RT1 and an analog-to-digital conversion module (not shown in the figure), and an output terminal of the potentiometer RT1 is coupled to an input terminal of the processor U1 through the analog-to-digital conversion module, and the processor U1 connects or disconnects the resistance control switch tube Q1 and the switch tube Q2 based on the potentiometer RT1. If a timer of the mosquito repeller cannot be set, the mosquito repeller will operate according to the working flow once when it is turned on. In other words, the mosquito repeller enters into the first time period, and then the second time period, and finally the third time period. In the present invention, the users can set the timer by adjusting the resistance of the potentiometer RT1, so that the mosquito repeller can start operating from the second time period or the third time period first. The processor U1 of the present invention comes with the analog-to-digital conversion module, so that the analog-to-digital conversion module is not shown in FIG. 3.

While the invention has been described by means of specific embodiments, numerous modifications and variations could be made thereto by those skilled in the art without departing from the scope and spirit of the invention as set forth in the claims.

What is claimed is:

1. A mosquito repeller, comprising: a casing, a mosquito repellent liquid bottle and a first heating element installed in the casing, wherein the first heating element-comprises a first heat-generating body and a cotton swab, the first heat-generating body is inserted into the cotton swab, the cotton swab extends from an end away from the first heat-generating body into the mosquito repellent liquid bottle, the casing comprises a first body, a second body, and a third body, the first body has a first end coupled to the second body and a second end coupled to the third body, and the mosquito repellent liquid bottle is disposed between the second body and the third body.

2. The mosquito repeller as claimed in claim 1, further comprising a fragrance liquid bottle, and a second heating element installed to the casing and extending into the fragrance liquid bottle.

3. The mosquito repeller as claimed in claim 1, wherein the mosquito repellent liquid bottle is coupled to the casing by a screw.

4. The mosquito repeller as claimed in claim 1, wherein the casing has a fastener, and the fastener has a first elastic plate and a second elastic plate which are provided for clamping the cotton swab.

5. The mosquito repeller as claimed in claim 1, wherein the casing has a through hole provided for an end of the cotton swab away from the mosquito repellent liquid bottle to be exposed from the casing.

6. The mosquito repeller as claimed in claim 2, wherein the second heating element has a second heat-generating body, the mosquito repeller further comprises a control circuit installed in the casing, and the control circuit comprises a first switch tube, a second switch tube and a processor, the first heat-generating body has a first end coupled to an external power supply and a second end grounded by the first switch tube, the second heat-generating body has a first end coupled to the external power supply and a second end grounded by the second switch tube, and the processor is provided for controlling connection and disconnection of the first switch tube and the second switch tube.

7. The mosquito repeller as claimed in claim 6, wherein the control circuit further comprises a potentiometer and an analog-to-digital conversion module, the potentiometer has an output terminal coupled to an input terminal of the processor through the analog-to-digital conversion module, and the processor connects or disconnects the first switch tube and the second switch tube based on the potentiometer.

* * * * *